(12) United States Patent
Wassinger et al.

(10) Patent No.: US 8,382,767 B2
(45) Date of Patent: Feb. 26, 2013

(54) IMPLANT INSERTION TOOL

(75) Inventors: Adam Wassinger, Reston, VA (US); Todd Wallenstein, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 323 days.

(21) Appl. No.: 12/610,822

(22) Filed: Nov. 2, 2009

(65) Prior Publication Data

US 2010/0114183 A1    May 6, 2010

Related U.S. Application Data

(60) Provisional application No. 61/110,320, filed on Oct. 31, 2008.

(51) Int. Cl.
*A61B 17/58* (2006.01)
*A61B 17/60* (2006.01)
*A61B 17/70* (2006.01)
*A61F 2/00* (2006.01)

(52) U.S. Cl. ........................ 606/99; 606/86 A; 606/914

(58) Field of Classification Search .............. 606/86 A, 606/99, 914
See application file for complete search history.

(56) References Cited

U.S. PATENT DOCUMENTS

| | | | |
|---|---|---|---|
| 3,486,505 A | 12/1969 | Morrison | |
| 3,762,400 A | 10/1973 | McDonald | |
| 3,848,601 A | 11/1974 | Ma et al. | |
| 3,960,147 A | 6/1976 | Murray | |
| 4,714,469 A | 12/1987 | Kenna | |
| 4,898,161 A | 2/1990 | Grundei | |
| 5,122,130 A | 6/1992 | Keller | |
| 5,431,658 A | 7/1995 | Moskovich | |
| 5,571,109 A | 11/1996 | Bertagnoli | |
| 5,599,279 A | 2/1997 | Slotman et al. | |
| 5,683,399 A | 11/1997 | Jones | |
| 5,704,937 A | 1/1998 | Martin | |
| 5,772,661 A | 6/1998 | Michelson | |
| 5,785,647 A | 7/1998 | Tompkins et al. | |
| 5,899,901 A | 5/1999 | Middleton | |
| 5,951,564 A | 9/1999 | Schroder et al. | |
| 6,017,342 A | 1/2000 | Rinner | |
| 6,063,088 A | 5/2000 | Winslow | |
| 6,096,038 A | 8/2000 | Michelson | |
| 6,159,215 A | 12/2000 | Urbahns | |
| 6,261,296 B1 | 7/2001 | Aebi et al. | |
| 6,436,119 B1 * | 8/2002 | Erb et al. | 606/198 |
| 6,478,800 B1 | 11/2002 | Fraser et al. | |
| 6,551,316 B1 | 4/2003 | Rinner et al. | |
| 6,569,168 B2 | 5/2003 | Lin | |
| 6,599,294 B2 | 7/2003 | Fuss et al. | |
| 6,616,671 B2 | 9/2003 | Landry et al. | |
| 6,652,533 B2 | 11/2003 | O'Neil | |
| 6,712,825 B2 | 3/2004 | Aebi et al. | |
| 6,755,841 B2 | 6/2004 | Fraser et al. | |

(Continued)

FOREIGN PATENT DOCUMENTS

| | | |
|---|---|---|
| EP | 0637439 | 2/1995 |
| EP | 1295578 | 3/2003 |

(Continued)

*Primary Examiner* — Sameh Boles
(74) *Attorney, Agent, or Firm* — Carter, DeLuca, Farrell & Schmidt, LLP

(57) ABSTRACT

An insertion tool for placing a spinal implant in an intervertebral space includes a handle assembly, a jaw assembly having first and second jaw members movable with respect to each other, and a holding member adapted to hold and release an implant in response to a manipulation of the handle assembly. The holding member is configured to move longitudinally with respect to the jaw assembly upon manipulation of the handle assembly.

6 Claims, 5 Drawing Sheets

U.S. PATENT DOCUMENTS

| | | |
|---|---|---|
| 6,770,074 B2 | 8/2004 | Michelson |
| 6,814,737 B2 | 11/2004 | Cauthen |
| 6,824,565 B2 | 11/2004 | Muhanna et al. |
| 6,887,248 B2 | 5/2005 | McKinley |
| 6,986,772 B2 | 1/2006 | Michelson |
| 7,070,598 B2 | 7/2006 | Lim et al. |
| 7,081,118 B2 | 7/2006 | Weber et al. |
| 7,087,055 B2 | 8/2006 | Lim et al. |
| 7,204,852 B2 | 4/2007 | Marnay |
| 7,294,134 B2 | 11/2007 | Weber |
| 7,419,505 B2 | 9/2008 | Fleischmann et al. |
| 7,455,639 B2 | 11/2008 | Ritland |
| 7,462,182 B2 | 12/2008 | Lim |
| 7,485,120 B2 | 2/2009 | Ray |
| 7,608,078 B2 | 10/2009 | Berry |
| 7,625,377 B2 | 12/2009 | Veldhuizen et al. |
| 7,625,379 B2 | 12/2009 | Puno et al. |
| 7,896,884 B2 | 3/2011 | Wing et al. |
| 2002/0116009 A1 | 8/2002 | Frader et al. |
| 2003/0055434 A1 | 3/2003 | O'Neil |
| 2003/0149438 A1 | 8/2003 | Nichols et al. |
| 2004/0002758 A1 | 1/2004 | Landry et al. |
| 2004/0030346 A1 | 2/2004 | Frey et al. |
| 2004/0225295 A1 | 11/2004 | Zubok |
| 2004/0267277 A1 | 12/2004 | Zannis et al. |
| 2005/0021042 A1 | 1/2005 | Marnay et al. |
| 2005/0113842 A1 | 5/2005 | Bertagnoli et al. |
| 2005/0119665 A1 | 6/2005 | Keller |
| 2005/0143747 A1 | 6/2005 | Zubok et al. |
| 2005/0165408 A1 | 7/2005 | Puno et al. |
| 2005/0182416 A1 | 8/2005 | Lim et al. |
| 2006/0030856 A1 | 2/2006 | Drewry et al. |
| 2006/0030857 A1 | 2/2006 | De Villiers et al. |
| 2006/0052793 A1 | 3/2006 | Heinz |
| 2006/0122701 A1 | 6/2006 | Kiester |
| 2006/0149284 A1 | 7/2006 | McCormack et al. |
| 2006/0235423 A1 | 10/2006 | Cantu |
| 2006/0241641 A1 | 10/2006 | Albans et al. |
| 2006/0241643 A1 | 10/2006 | Lim et al. |
| 2007/0016220 A1 | 1/2007 | Michelson |
| 2007/0016221 A1 | 1/2007 | Beyersdorff et al. |
| 2007/0123901 A1 | 5/2007 | Foley et al. |
| 2007/0123903 A1 | 5/2007 | Raymond et al. |
| 2007/0123904 A1 | 5/2007 | Stad et al. |
| 2007/0191857 A1 | 8/2007 | Allard et al. |
| 2007/0198025 A1 | 8/2007 | Trieu et al. |
| 2007/0233143 A1 | 10/2007 | Josse et al. |
| 2007/0260315 A1 | 11/2007 | Foley et al. |
| 2008/0045968 A1 | 2/2008 | Yu et al. |
| 2008/0077153 A1 | 3/2008 | Pernsteiner et al. |
| 2008/0161817 A1 | 7/2008 | Parsons et al. |
| 2008/0177275 A1 | 7/2008 | Wing et al. |
| 2008/0275455 A1 | 11/2008 | Berry et al. |
| 2008/0287957 A1 | 11/2008 | Hester et al. |
| 2008/0306488 A1 | 12/2008 | Altarac et al. |
| 2009/0030422 A1 | 1/2009 | Parsons et al. |
| 2009/0048604 A1 * | 2/2009 | Milz et al. .................... 606/99 |
| 2010/0069914 A1 | 3/2010 | Puno et al. |
| 2010/0249792 A1 | 9/2010 | Bonvallet et al. |

FOREIGN PATENT DOCUMENTS

| | | |
|---|---|---|
| EP | 1323396 | 7/2003 |
| WO | WO 2004/066884 | 8/2004 |
| WO | WO/2004066884 | 8/2004 |
| WO | WO/2005072662 | 8/2005 |

* cited by examiner

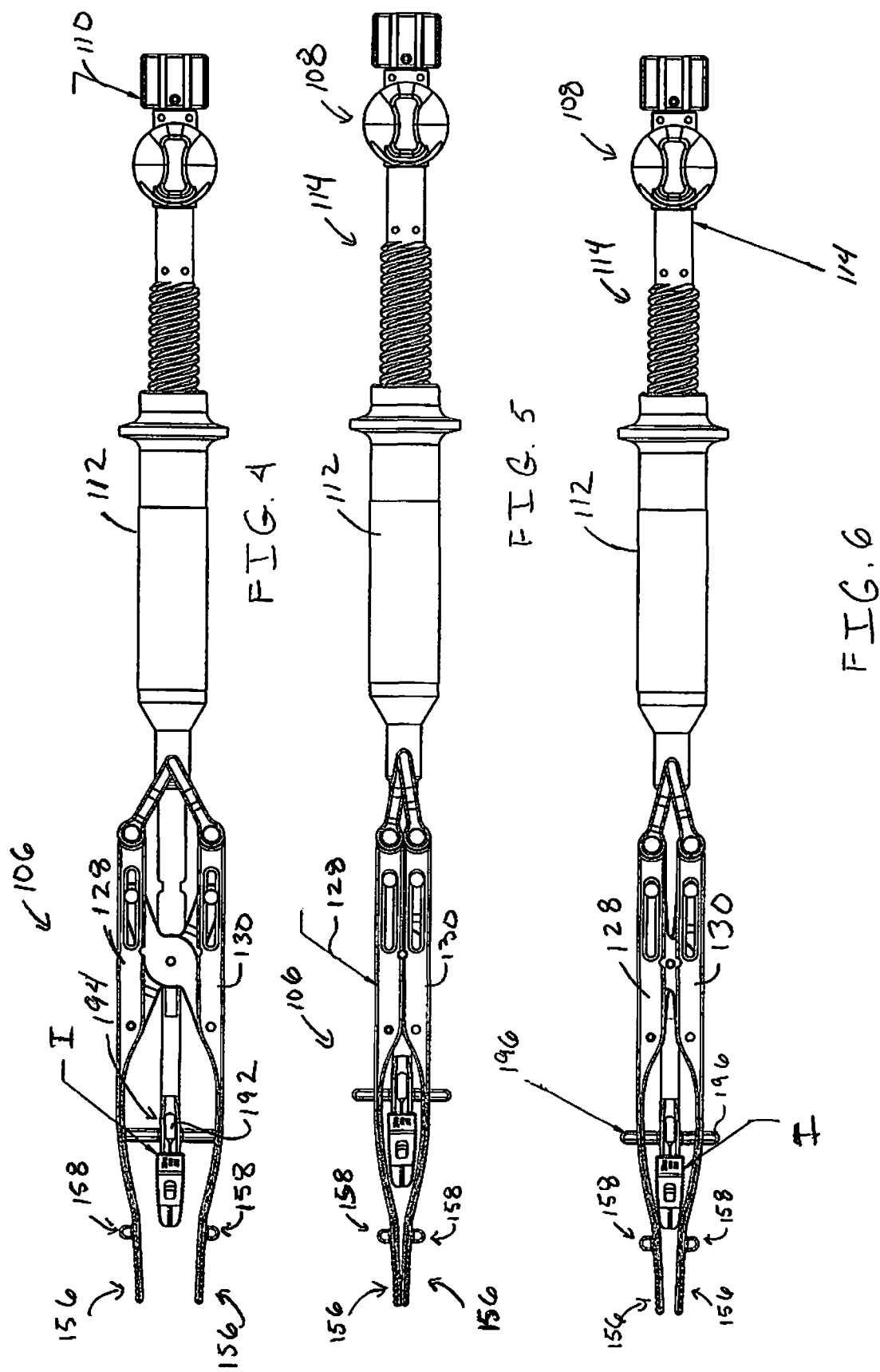

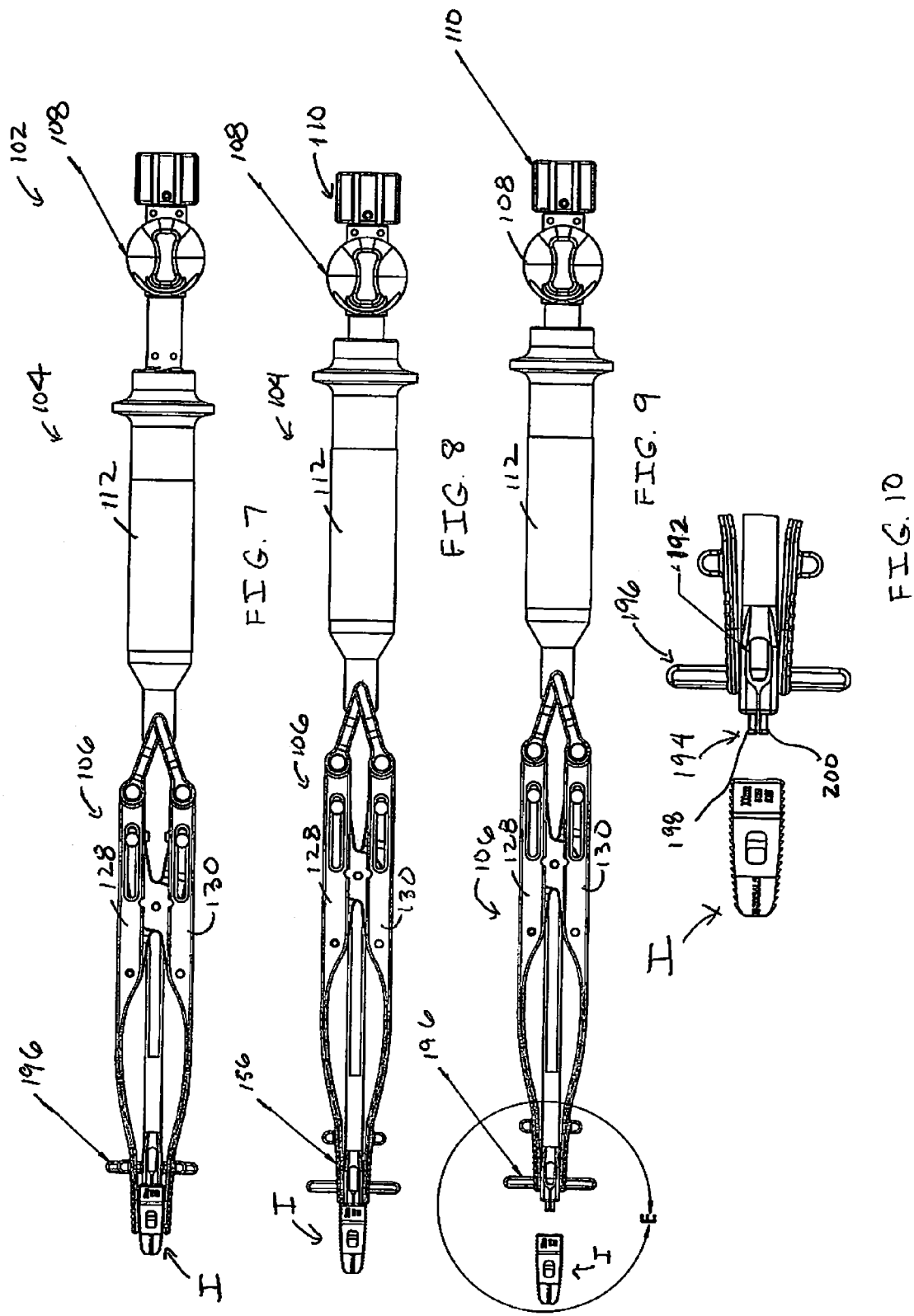

IMPLANT INSERTION TOOL

CROSS-REFERENCE TO RELATED APPLICATIONS

The present application claims priority to, and the benefit of, U.S. Provisional Patent Application Ser. No. 61/110,320, filed Oct. 31, 2008, the entire contents of which are hereby incorporated by reference.

BACKGROUND

1. Technical Field

The present disclosure relates to apparatus and methods for orthopedic spine surgery and, in particular, to apparatus for inserting an implant into an intervertebral space.

2. Background of Related Art

The human spine is comprised of thirty-three vertebrae and twenty-four as an adult. An infant contains 7 cervical vertebrae, 12 dorsal or thoracic vertebrae, 5 lumbar vertebrae, 5 sacral vertebrae, and 4 coccygeal or caudal vertebrae. In an adult, the 5 sacral vertebrae fuse together to form the sacrum and the 4 coccygeal vertebrae fuse to form the coccyx. Intervertebral discs lie between each pair of adjacent vertebrae. Every intervertebral disc maintains a space between adjacent vertebrae and acts as cushion under compressive, bending, and rotational loads and motions. Each intervertebral disc has a fibrocartilaginous central portion called the nucleus pulposus. The nucleus pulposus of a healthy intervertebral disc contains significant amount of water. This water content provides spongy quality and allows it to absorb spinal stress.

Each intervertebral disc has an annulus fibrosus, which condition might be affected by the water content of the nucleus pulposus. The annulus fibrosus consist of a ring of fibrocartilage and fibrous tissue forming the circumference of the intervertebral disc. Excessive pressure or injuries to the intervertebral discs may adversely affect the annulus fibrosus. Usually, the annulus fibrosus is the first portion of the intervertebral discs that is injured. The annulus fibrosus may be injured in several ways. Typically, the annulus fibrosus tears due to an injury. When these tears heal, scar tissue forms in the annulus fibrosus. Given that scar tissue is not as strong as normal ligament tissue, the annulus becomes weaker as more scar tissue forms. An annulus fibrosus with scar tissue is usually weaker than a normal annulus fibrosus. The formation of scar tissue may eventually lead to damage to the nucleus pulposus. As a result of this damage, the nucleus fibrosus may, for instance, lose water content, hindering the intervertebral disc's ability to act as a cushion. The reduced cushioning capability might increase stresses on the annulus fibrosus and, consequently, cause still more tears. Hence, the annulus fibrosus may undergo a degenerative cycle consisting of exponential reduction of water content. Eventually, the nucleus pulposus may lose all its water. As the nucleus pulposus loses its water content, it collapses and thus allows the vertebrae above and below the disc space to move closer to each other. In other words, the intervertebral disc space narrows as the nucleus pulposus loses water. When the nucleus pulposus collapses, the facet joints, which are located on the back of the spine, shift, altering the way these joints work together.

When a disc or vertebra is damaged due to disease or injury, performing a spinal fusion is one of the techniques used for treating the patient. During spinal fusion, a surgeon removes part or all of the intervertebral disc, inserts a natural or artificial disc spacer, and constructs an artificial structure to hold the affected vertebrae in place. While the spinal fusion may address the diseased or injured anatomy, the natural biomechanics of the spine are affected in a unique and unpredictable way.

SUMMARY

The present disclosure relates to an insertion tool for placing a spinal implant in an intervertebral space. The insertion tool includes a handle assembly, a jaw assembly having first and second jaw members movable with respect to each other, and a holding member adapted to hold and release an implant in response to a manipulation of the handle assembly. The holding member is configured to move longitudinally with respect to the jaw assembly upon manipulation of the handle assembly.

BRIEF DESCRIPTION OF THE DRAWINGS

Embodiments of the presently disclosed insertion tool are disclosed herein with reference to the drawings, wherein:

FIG. 4 is a side view of the insertion tool shown in FIG. 1A in an open position and holding a spinal implant;

FIG. 5 is a side view of the insertion tool shown in FIG. 1A in a closed position and holding the spinal implant;

FIG. 6 is a side view of the insertion tool shown in FIG. 1A with the spinal implant advancing through the insertion tool;

FIG. 7 is a side view of the insertion tool shown in FIG. 1A with the spinal implant partially advanced through the insertion tool;

FIG. 8 is a side view of the insertion tool shown in FIG. 1A with the spinal implant fully advanced through the insertion tool;

FIG. 9 is a side view of the insertion tool shown in FIG. 1A with the spinal implant separated from the insertion tool; and FIG. 10 is a side sectional view of the insertion tool shown in FIG. 1A with the spinal implant separated from the insertion tool, taken around section E of FIG. 9.

DETAILED DESCRIPTION OF THE EMBODIMENTS

Figure 1:
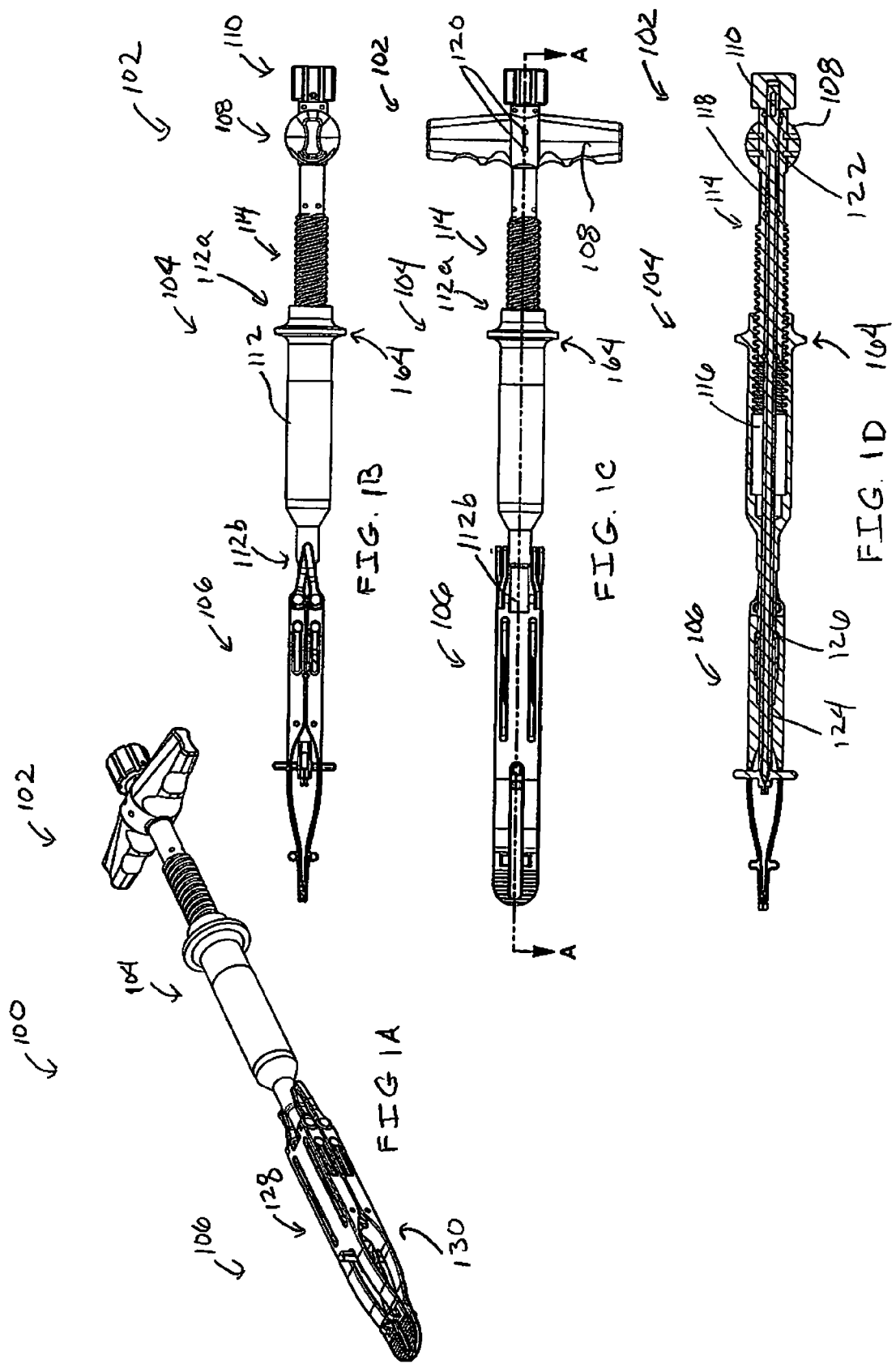
FIG. 1A is a perspective view of an insertion tool in a closed position according to an embodiment of the present disclosure.
FIG. 1B is a side view of the insertion tool shown in FIG. 1A.
FIG. 1C is a top view of the insertion tool shown in FIG. 1A.
FIG. 1D is a side cross-sectional view of the insertion tool shown in FIG. 1A, taken along section line A-A of FIG. 1C.
Figure 2:
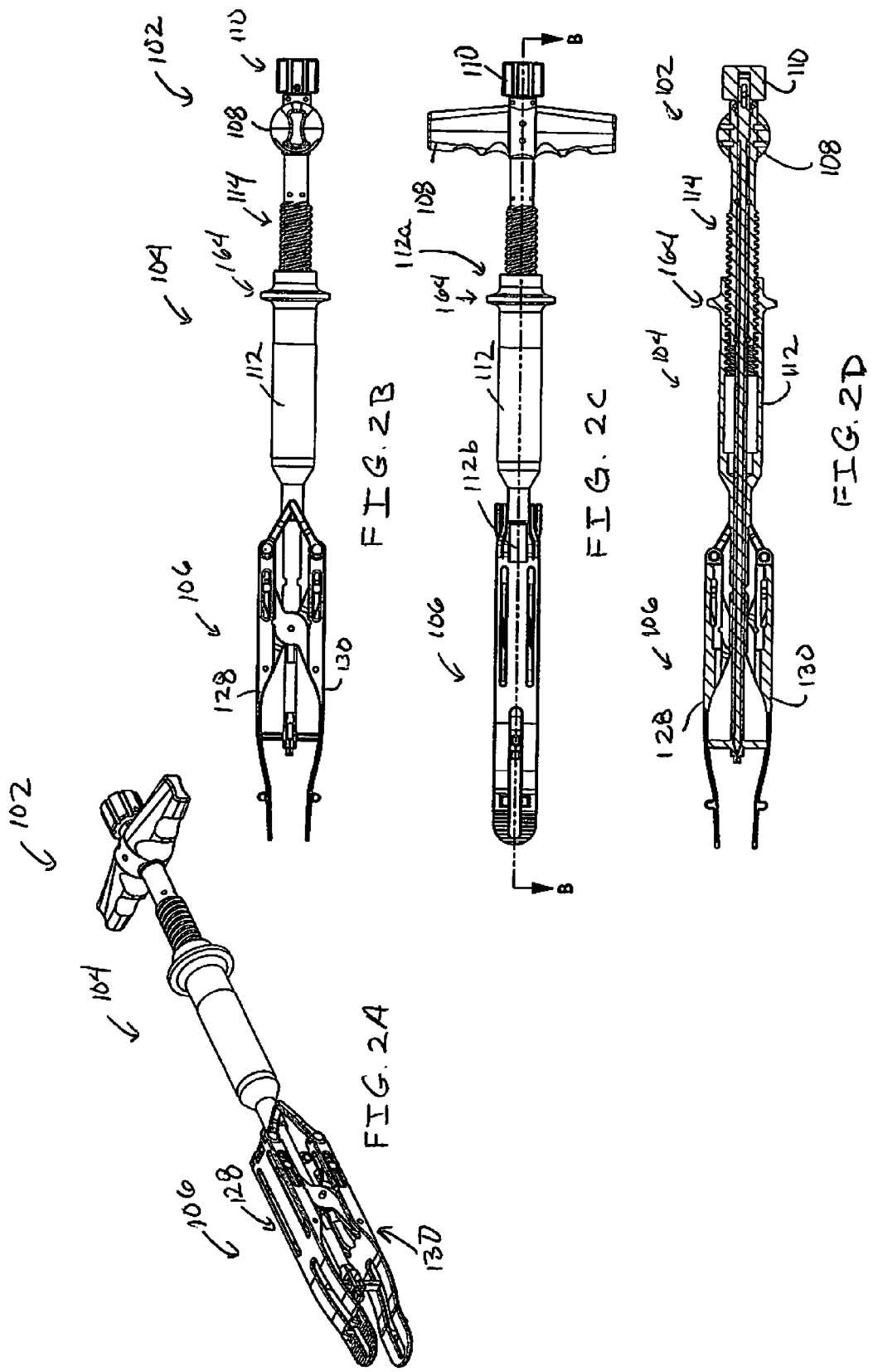
FIG. 2A is a perspective view of the insertion tool illustrated in FIG. 1A in an open position.
FIG. 2B is a side view of the insertion tool shown in FIG. 2A.
FIG. 2C is a top view of the insertion tool shown in FIG. 2A.
FIG. 2D is a side cross-sectional view of the insertion tool shown in FIG. 2A, taken along section line B-B of FIG. 2C.

Embodiments of the presently disclosed insertion tool will now be described in detail with reference to the drawings in which like reference numerals designate identical or corresponding elements in each of the several views. In the description, the term "proximal" will refer to the portion of the insertion tool that is closest to the operator, while the term "distal" will refer to the portion of the insertion tool that is farthest from the operator.

FIGS. 1A-1D show an insertion tool 100 adapted for placing an orthopedic device, such as a spinal implant "I" (FIG. 6), inside a patient's body. Insertion tool 100 generally includes a handle assembly 102, an elongate portion 104, and a jaw assembly 106 disposed adjacent to the elongate portion 104. In operation, insertion tool 100 facilitates insertion of the spinal implant "I" into an intervertebral space located between adjacent vertebrae. Insertion of the spinal implant "I" is achieved through manipulation of handle assembly 102.

Handle assembly 102 includes a handle 108 mounted on elongate portion 104 and a knob 110 disposed proximally relative to handle 108. Elongate portion 104 features a housing 112 and a tubular member 114 dimensioned for positioning within housing 112. Housing 112 defines a bore 116 configured to receive tubular member 114 and has internal thread disposed around bore 116. Tubular member 114 includes an external thread and defines a bore 118 therein. The external thread of tubular member 114 is adapted for threadably engaging the internal thread of housing 112.

The threaded engagement between tubular member 114 and housing 112 allows tubular member 114 to move longitudinally relative to housing 112 upon rotation of tubular member 114 with respect to housing 112. In operation, a user can rotate tubular member 114 through manual manipulation of handle 108. Handle 108 is mounted on tubular member 114. In certain embodiments, a series of pins 120 secure handle 108 to tubular member 114. Said secure connection permits rotation of tubular member 114 via a corresponding rotation of handle 108.

Aside from handle 108, handle assembly 102 includes a knob 110 positioned proximally in relation to handle 108. Knob 110 is rotatably coupled to a tube 122 located within tubular member 114. Tube 122 operatively interconnects knob 110 and a hollow rod 124. Hollow rod 124 is partially positioned in bore 118 of tubular member 114 and defines a lumen 126 extending therethrough. Lumen 126 is configured to receive tube 122. As seen in FIG. 1D, a proximal portion of hollow rod 124 is located inside housing 112 and a distal portion of hollow rod 124 is positioned outside of housing 112.

Figure 3:
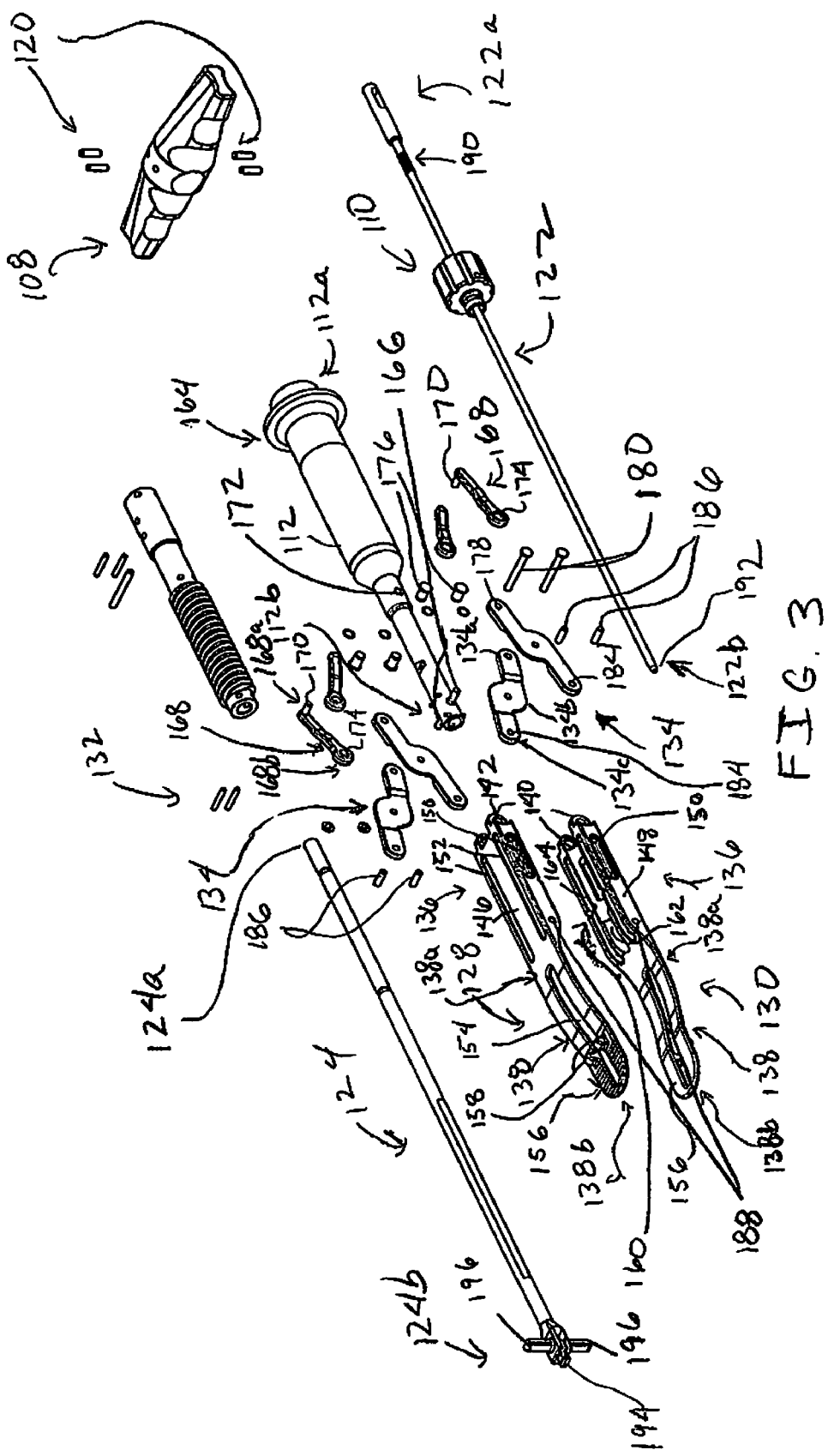
FIG. 3 is an exploded perspective view of the insertion tool shown in FIG. 1A.

Referring briefly to FIG. 3, housing 112 further includes a flange 164 located around a proximal end 112a thereof and pivot pins 166 extending radially from a distal portion 112b thereof. The cross-sectional area of housing 112 varies along its length. In the illustrated embodiment, the proximal portion 112a of housing 112 has a larger cross-sectional area than the distal portion 112b of housing 112.

Returning to FIGS. 1A-1D, jaw assembly 106 is connected to a distal portion 112b of housing 112 and includes first and second jaw members 128, 130 movable with respect to each other. A pivot mechanism 132 pivotally couples first and second jaw members 128, 130. In operation, pivot mechanism 132 allows first and second jaw members 128, 130 to move between a closed position, as seen in FIGS. 1A-1D, and an open position as depicted in FIGS. 2A-2D. In the closed position, first and second jaw members 128, 130 are juxtaposed, whereas, in the open position, first and second jaw members 128, 130 are spaced apart from one another.

With reference to FIG. 3, each jaw member 128, 130 has a connecting portion 136 disposed on a proximal portion thereof and a jaw extension 138 protruding distally from connecting portion 136. Connecting portion 136 has an elongate profile and includes a pair of rims 140 each extending proximally therefrom. Each rim 140 defines a hole 142. In addition to rims 140, connecting portion 136 includes a top wall 146 and two side walls 148 arranged in a diametrically opposed relation to each other. Each side wall 148 is connected to a top wall 146 and includes longitudinal slot 150. Top wall 146 has a pair of longitudinal slot 152 oriented in a substantially parallel relation to each other. Connecting portion 136 additionally includes an interior wall 160 oriented in a diametrically opposed relation to top wall 146. Interior wall 160 defines a central groove 162 and two lateral grooves 164. Each lateral groove 164 leads to a corresponding longitudinal slot 152 formed on top wall 146.

A jaw extension 138 obtrudes from each top wall 146 of each connecting portion 136. As discussed above, each jaw member 128, 130 includes a jaw extension 138. Jaw extension 138 may have any suitable shape or configuration. In the embodiment depicted in FIG. 3, jaw extension 138 features a curved profile and contains a slot 154 extending longitudinally therealong. Specifically, slot 154 extends from a proximal portion 138a to a distal portion 138b of jaw extension 138. Each jaw extension 138 further includes a jaw tip 156 having a rugged outer surface. In use, the rugged outer surface of each jaw tip 156 increases the coefficient of friction between adjacent vertebrae and jaw tips 156. Besides jaw tip 156, each jaw extension 138 includes two mechanical stops 158 located on opposite sides of slot 154. Mechanical stop 158 limits the advancement of jaw extensions 138 into the intervertebral space between adjacent vertebrae.

With continued reference to FIG. 3, insertion tool 100 includes pivot mechanism 132 for facilitating pivotal movement of first and second jaw members 128, 130. Through said pivotal movement, first and second jaw members 128, 130 move between the open position, as shown in FIGS. 2A-2D, and the closed position, as seen in FIGS. 1A-1D. Pivot mechanism 132 includes a plurality of pivot bars 134 pivotally connecting first and second jaw members 128, 130 and pivot struts 168 pivotally connecting each of the first and second jaw members 128, 130 to housing 112. In some embodiments, pivot struts 168 contain a distal end 168b adapted for connection to rim 140 of connecting portion 13 and a proximal end 168a adapted for connection to housing 112. Proximal end 168a of pivot struts 168 include pins 170 extending radially toward housing 112. Pins 170 are configured to be pivotally received by holes 172 located between the proximal and distal ends 112a, 112b of housing 112. Distal ends 168b of each pivot struts 168 include an opening 174 aligned with hole 142 of each rim 140. A pivot pin 176 extends through hole 142 of each rim 140 and opening 174 of each pivot struts 168 to pivotally connect first and second jaw members 128, 130 with housing 112.

Pivot bars 134 each include a proximal portion 134a, a central portion 134b, and a distal portion 134c. Central portion 134b is located between proximal and distal portions 134a, 134c. Proximal portion 134a includes a hole 178 adapted to receive a sliding pin 180. Each sliding pin 180 passes through hole 178 of pivot bar 134 and longitudinal slot 150 of each of the jaw members 128, 130 to pivotally secure jaw members 128, 130 to pivot bars 134. In particular, each sliding pin 180 is slidably disposed in a longitudinal slot 150 such that, during operation, sliding pin 180 slides longitudinally along slot 150, while pivot bar 134 pivots about its central portion 134b, causing first and second jaw members 128, 130 to move between open and closed positions in a substantially parallel arrangement.

Central portions 134b of pivot bar 134 each include a hole 182 adapted to receive a pivot pin 166 of housing 112. As discussed above, pivot pins 166 are positioned on distal end 112b of housing 112. In operation, each pivot bar 164 pivots about pivot pin 166, thereby moving first and second jaw members 128, 130 between the open and closed positions.

Each proximal portion 134c of pivot bars 134 includes a hole 184 adapted to receive pins 186. Side walls 148 of first and second jaw members 128, 132 each have openings 188 adapted to receive pins 186 as well. Pins 186 pass through hole 184 of pivot bar 134 and opening 188 of first and second jaw members 128, 130, pivotally securing pivot bar 134 to first and second jaw members 128, 130.

Lateral grooves 164 of first and second jaw members 128, 130 receive pivot bars 134, whereas central groove 162 receives hollow rod 124 and distal end 112b of housing 112. As previously discussed, housing 112 partially encompasses hollow rod 124. Hollow rod 124 in turn partially surrounds tube 122 and has a proximal portion 124a and a distal portion 124b. Proximal portion 124b is positioned inside housing 112, while distal portion 124b is disposed between first and second jaw members 128, 130. Tube 122 also has a proximal portion 122a and a distal end 122b. Proximal portion 122a of tube 122 includes an external thread formed thereabout for threadably engaging proximal portion 124a of hollow rod 124. Knob 110 is mounted on proximal portion 122a of tube 122 so that rotation of knob 110 causes a corresponding rotation of tube 122. Tube 122 is also capable of translating along lumen 126 of hollow rod 124. Distal portion 122b of tube 122 features a plunger 192 for spreading a holding member 194 of hollow rod 124.

As seen in FIG. 10, distal portion 124 includes a holding member 194 and a pair of extended protrusions 196 extending radially therefrom. Holding member 194 includes first and second movable parts or fingers 198, 200 capable of moving away and toward each other in response to an engagement of plunger 192. Specifically, first and second movable parts move away from each other, when plunger 192 engages holding member 194. Conversely, first and second movable parts 198, 200 move toward each other when plunger 192 is released from holding member 192. When first and second movable parts 198, 200 are positioned inside implant "I," holding member 194 holds implant "I" when first and second movable parts 198, 200 are spread apart from each other due to the pressure exerted by plunger 192 on holding member 194. Once first and second movable parts 198, 200 are separated from each other, first and second movable parts 198, 200 securely engage the inner portions of implant "I." Implant "I" can be released from holding member 194 by moving plunger 192 away from holding member 194, thereby moving first and second movable parts 198, 200 toward each other. When first and second movable parts 198, 200 move toward each other, first and second movable parts 198, 200 disengage the inner portions of implant "I."

As shown in FIGS. 6-10, insertion tool 100 facilitates insertion of the implant "I" into an intervertebral space during a surgical operation. Initially, a surgeon mounts implant "I" on holding member 194, while the jaw assembly 106 is in the open position as seen in FIG. 4. The surgeon then rotates knob 110 to move plunger 192 toward holding member 194 until plunger 192 engages holding member 194. As plunger 192 engages holding member 194, first and second movable parts 198, 200 (see FIG. 10) of holding member 194 move away from each other and securely engage inner portions of implant "I." Once first and second movable parts 198, 200 of holding member 194 engage implant "I," holding member 194 securely holds implant "I." After securing implant "I" to insertion tool 100, the surgeon moves jaw assembly 106 to the closed position as illustrated in FIG. 5. When jaw assembly 106 is in the closed position, first and second jaw members 128, 130 are juxtaposed to each other. The surgeon then creates an access to the target surgical site using known techniques and instruments. After making the access to the vertebra, the surgeon removes at least part of an intervertebral disc to create space for the implant. The jaw tips 156 of first and second jaw members 128, 132 are then inserted in the intervertebral space created by the surgeon. The surgeon advances insertion tool 100 toward the adjacent vertebrae until mechanical stops 158 press against the vertebra bodies of the adjacent vertebrae. The surgeon subsequently rotates handle 108 to thread tubular member 114 in a distal direction as depicted in FIG. 6. As a result of the distal movement of tubular member 114, hollow rod 124 moves distally. Since holding member 192 is part of hollow rod 124, holding member 192 also moves distally as tubular member 114 moves distally, thereby pushing implant "I" distally. While implant "I" translates distally, implant "I" acts as a wedge and spreads apart first and second jaw members 128, 130 as seen in FIG. 6. In addition, extended protrusions 196 move distally along slots 154 (see FIG. 3) as holding member 192 moves distally, thus providing visual indication of the position of the implant "I" relative to the jaw assembly 106. In an alternate embodiment, as implant "I" translates distally, the jaw members 128, 130 move away from each other in a substantially parallel direction, thereby distracting the adjacent vertebrae. Once the desired space is created between the adjacent vertebrae, the spinal implant "I" is advanced into the space and separated from the insertion tool 100. Subsequently, the jaw members 128, 130 are approximated towards each other and the insertion tool 100 is removed. In all contemplated embodiments, the jaw members 128, 130 move toward each other and away from each other in a substantially parallel arrangement.

As illustrated in FIG. 7, the surgeon continues threading tubular member 114 through handle 108 to move holding member 194 along with implant "I" distally toward the intervertebral space created between adjacent vertebrae. During the distal translation of holding member 194, extended protrusions push against the vertebral bodies of the adjacent vertebrae, thereby pulling insertion tool 100 out of the intervertebral disc space. Continued distal translation of holding member 194 causes implant "I" to begin exiting jaw assembly 106 as shown in FIG. 7. Once implant "I" completely exits jaw assembly 106, first and second jaw members 128, 130 automatically return to their closed position as illustrated in FIG. 8. After the implant "I" is placed in the desired surgical site, the surgeon rotates knob 110 to release implant "I" from holding member 194 as depicted in FIG. 9. A rotation of knob 110 causes plunger 192 to move proximally. When plunger 192 moves proximally, first and second movable parts 198, 200 of holding member 194 move toward each other, disengaging implant "I" from holding member 194. In an alternate embodiment, where the spinal implant "I" does not cam against the jaw members 128, 130, the insertion tool 100 is actuated to close the jaw members 128, 130 towards each other prior to removal of the insertion tool 100.

It will be understood that various modifications may be made to the embodiments of the presently disclosed insertion tool. Therefore, the above description should not be construed as limiting, but merely as exemplifications of embodiments. Those skilled in the art will envision other modifications within the scope and spirit of the present disclosure.

What is claimed is:

1. A surgical system comprising: an implant; a housing having a first bore extending therethrough, at least a portion of the first bore including threads; an elongate tubular member including threads formed thereon, the threads adapted for threadably engaging the threads of the first bore; a handle assembly disposed at a first end of the elongate tubular member, the handle assembly including a handle and a knob, the knob being rotatable relative to the elongate tubular member; a tube rotatably coupled to the knob; a hollow rod partially disposed in the elongate tubular member, the tube disposed within the hollow rod, the hollow rod including a distal portion configured and adapted for releasably engaging the implant, the distal portion of the hollow rod including opposed fingers that are repositionable between an open condition and a closed condition, the tube being axially repositionable relative to the hollow rod such that when a distal end of the tube engages the fingers of the hollow rod, continued distal movement of the tube urges the fingers towards the open condition such that the fingers engage the implant and retain the implant on the hollow rod; and an end effector coupled to the housing, the end effector including: a first jaw member, a second jaw member, the jaw members coupled to one another such that distal translation of the implant causes the first and second jaws to move between open and closed positions in a substantially parallel arrangement with respect to a longitudinal axis of the handle; a pivot mechanism comprising: a first bar movably coupled to the first and second jaw members; and a second bar movably coupled to the first and second jaw members, the second bar pivotally coupled to the first bar such that the first and second jaw members move apart in parallel; a first strut pivotally coupled to a proximal end of the first jaw member and the housing; and a second strut pivotally coupled to a proximal end of the second jaw member and the housing.

2. The surgical system of claim 1, wherein rotation of the handle in a first direction advances the hollow rod relative to the housing.

3. The surgical system of claim 1, further including visual indication of the position of the implant.

4. The surgical system of claim 1, wherein the first and second jaw members are adapted for insertion between adjacent vertebrae when the first and second jaw members are in close cooperative alignment.

5. The surgical system of claim 1, wherein as the implant advances distally relative to the end effector, movement of the first and second jaws result in distraction of an intervertebral space between adjacent vertebrae.

6. The surgical system of claim 1, wherein the distal translation of the implant urges the first jaw member to move a first distance and the second jaw member to move a second distance, wherein the second distance is substantially equal to the first distance.

* * * * *